United States Patent [19]

Cosentino et al.

[11] 4,068,521
[45] Jan. 17, 1978

[54] ULTRASONIC AIR AND BLOOD FOAM DETECTOR

[75] Inventors: Louis C. Cosentino, Wayzata; LeRoy J. Fischbach, Minneapolis, both of Minn.

[73] Assignee: Renal Systems, Inc., Minneapolis, Minn.

[21] Appl. No.: 707,485

[22] Filed: July 22, 1976

[51] Int. Cl.² ............................................. G01N 7/00
[52] U.S. Cl. ........................................ 73/19; 128/2 V
[58] Field of Search ..................... 73/19, 67.6, 67.5 R; 128/2 V

[56] References Cited

U.S. PATENT DOCUMENTS 3,921,622  11/1975  Cole ..................................... 73/19 X
3,974,681  8/1976  Namery ............................... 73/19 X Primary Examiner—Jerry W. Myracle
Attorney, Agent, or Firm—Schroeder, Siegfried, Ryan, Vidas & Steffey

[57] ABSTRACT

An ultrasonic air and blood foam detector for use in medical procedures involving extracorporeal handling of blood. A sensor assembly is adapted for positioning about a blood drip chamber and contains ultrasonic transducer means. The blood tube downstream from the drip chamber is preferably placed through the controllable clamp. Electronic circuitry provides excitation to the ultrasonic transducer means and signals transmitted through the chamber are received, amplified and processed by a level detector which provides an output signal for actuating the clamp when a predetermined low signal level occurs, indicating excessive air or foam in the drip chamber. In the preferred embodiment, a clip-on sensor assembly having epoxy lenses is provided.

17 Claims, 10 Drawing Figures

ULTRASONIC AIR AND BLOOD FOAM DETECTOR

BACKGROUND OF THE INVENTION

The present invention pertains to improvements in air leak detectors for use in the medical field. Many medical and surgical procedures require that the patient's blood be transported outside the patient's body, for example for connection to a heart-lung machine during surgery, or to an artificial kidney machine during hemodialysis. This extracorporeal transportation of blood is accomplished by means of blood tubing, with appropriate pumps, fittings, valves, etc. that may be required depending upon the particular procedure involved.

In the case of hemodialysis, the patient's blood is conveyed to the dialyzer by means of a length of tubing and a blood access device which connects the tubing to an artery. After purification by the dialyzer, the blood is returned through additional tubing to the patient. In addition to the dialyzer, the external blood flow path may include additional elements such as a pump and pressure monitors.

It will be appreciated that should an air leak develop anywhere in the external blood flow path, including the tubing, connectors, dialyzer, or heart-lung machine in the case of certain types of surgery, air would be allowed to enter the tubing. If a large air bubble were allowed to return with the blood to the patient's body, the result could be fatal. In order to prevent such occurrence, drip chambers are usually connected in the blood return path to the patient, to remove any air or other undissolved bubbles in the blood. In addition, good practice requires the use of some type of air leak detector, either on the drip chamber, on the blood tubing just prior to the return point to the patient's vein. It is also important that a clamping device working in conjunction with the sensor be provided for positively cutting off the flow upon detection of excessive air in the line.

Air leak detectors with spring-loaded clamps are disclosed in U.S. Pat. No. 3,935,876, issued Feb. 3, 1976, and assigned to the same assignee as the present invention. In that patent, air bubbles are detected and integrated, and a spring-loaded clamp is released to pinch off the blood tube when an excessive amount of air is detected.

In the preferred embodiment disclosed in U.S. Pat. No. 3,935,876, optical sensing is used for the detection of air bubbles, and some type of optical sensing has been used on most prior art air leak detectors, either on the blood tubing or on a drip chamber. One problem with optical sensing is that it is very difficult to get the light to penetrate more than a short distance into the blood, so that air bubbles passing through the center of a flow stream may not be detected. A more serious problem with optical sensing for drip chambers is the difficulty in distinguishing between blood or foam.

The possibility of accidental introduction of large quantities of blood foam is a major clinical problem in certain types of hemodialysis procedures. It is possible that air leaking into a blood line at a fistula connection prior to a pump would be converted into microfoam upon passing through a hollow fiber dialyzer. Microfoam can involve a substantial volume of air which is distributed in a tremendous number of extremely small air bubbles of less than 50 microliters each. This type of microfoam is essentially undetectable by any known optical sensing technique, and in fact may not even be visible to the eye of a careful observer.

Ultrasonic sensing has therefore been proposed for detecting air in drip chambers, since under favorable conditions, ultrasonic techniques can penetrate the blood, and can distinguish between blood and foam. However, the ultrasonic techniques which have heretofore been proposed have certain problem areas. One problem area is the difficulty of insuring good ultrasonic conduction between the plastic walls of the drip chamber and the transducers. In other types of ultrasonic measurement systems the transducers must be coated with an acoustically conducting gel, but this technique is undesirable in a clinical setting. Another problem area is the difficulty of maintaining accurate measurements in a system which attempts to measure pulse propagation time through the blood, due to the relatively small percentage change in propagation time caused by introduction of small air bubbles, and due to the difficulty of maintaining precise, repeatable spacing between sensors.

SUMMARY OF THE INVENTION

The present invention overcomes these and other problems by providing an improved ultrasonic air and blood foam detector for use on a drip chamber of a blood tube system. The detector according to the present invention includes ultrasonic sensing means for positioning adjacent the blood drip chamber and having ultrasonic transducer means positioned for good acoustic contact with the walls of the drip chamber, when the sensing means is positioned adjacent the drip chamber. Energization means connected to the transducer means causes ultrasonic energy to be transmitted and received through the blood drip chamber. Electronic signal level detection means connected to the transducer means receives signals transmitted through the blood drip chamber and operate in response to the signal level thereof to produce an output signal indicative of the presence of air or blood foam in the chamber.

In a preferred embodiment, the output signal indicative of the presence of air is used to control the operation of tube clamp means for selectively clamping an output tube from the drip chamber so as to prevent flow therethrough when excessive air or foam is detected.

The preferred ultrasonic sensor assembly for use in the present invention includes a pair of body member slideably interconnected, the body members forming a drip chamber receiving area therebetween. An ultrasonic transducer crystal is mounted in at least one of the body members, and a layer of polymeric material on the transducer crystal is shaped to form a lens for ultrasonic energy, and is positioned for contacting the side of a blood drip chamber when positioned in the receiving area.

DETAILED DESCRIPTION OF THE PREFERRED EMBODIMENT

Figure 1:
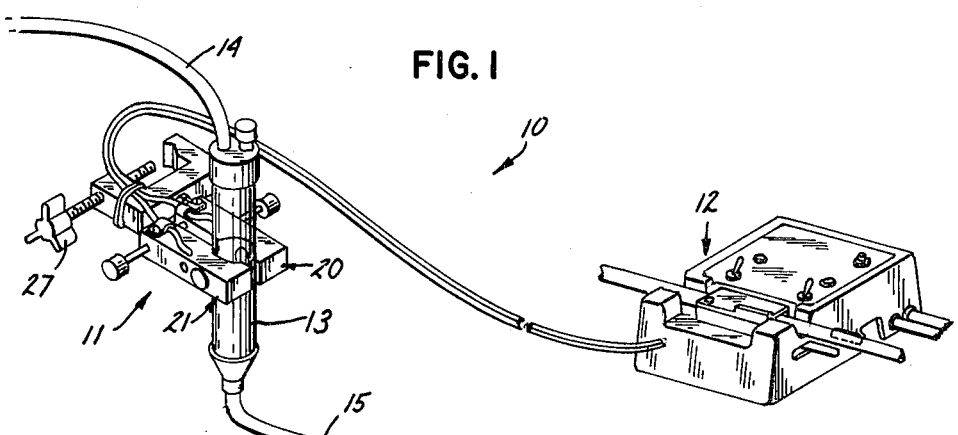
FIG. 1 is a view in perspective of a detector according to the present invention.

Referring to FIG. 1, reference numeral 10 generally designates the ultrasonic air leak detector according to the present invention. The detector includes a sensor assembly 11, and a chassis 12 which includes the tube clamping means and electronic circuitry. The sensor assembly is shown positioned about a drip chamber 13. Blood tubes 14 and 15 are the return line for blood from the external loop to the patient, and drip chamber 13 is inserted in this line. In FIG. 1, blood tube 15 is shown broken away, but it will be understood that blood tube 15 passes through a tube receiving channel in the chassis 12 just prior to the return connection to the patient.

Figure 2:
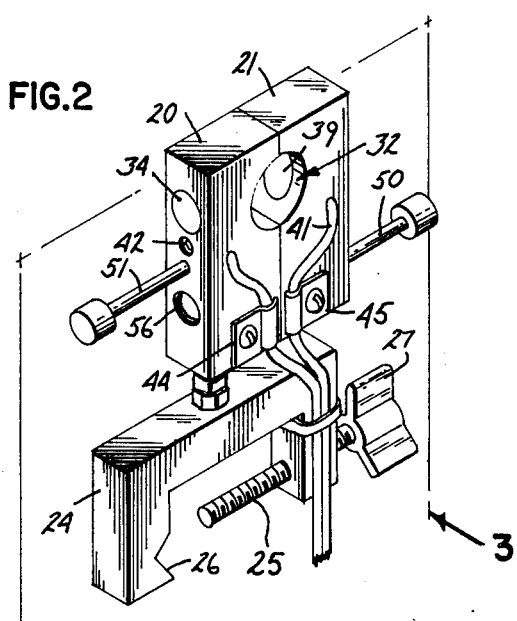
FIG. 2 is a view in perspective of the sensor assembly shown in FIG. 1.

The sensor mounting assembly is shown in greater detail in FIG. 2. In use, the sensor assembly would ordinarily be oriented as in FIG. 1 so as to hold the drip chamber in a vertical orientation; the different orientation of the sensor assembly in FIG. 2 is for purposes of clarity.

Figure 3:
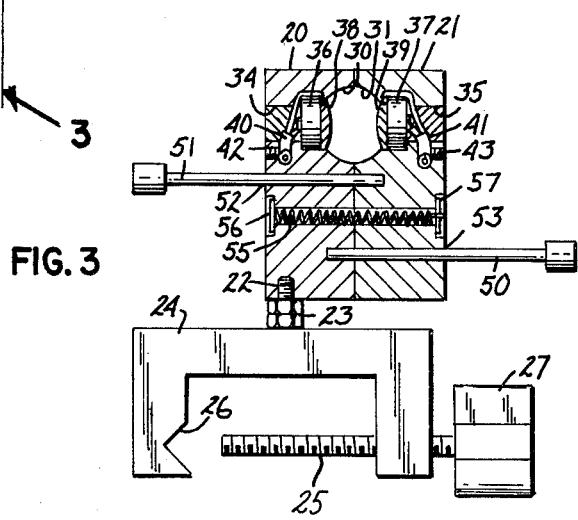
FIG. 3 is a sectional view taken generally along the line 3—3 of FIG. 2.

As seen in FIGS. 2 and 3, the sensor assembly comprises a pair of generally rectangular sensor blocks 20 and 21, which are positioned adjacent each other along facing edges thereof. Blocks 20 and 21 may be made of any suitable material, and in the preferred embodiment acetal copolymer is used. For convenience, one of the blocks, for example block 20, may be attached to a mounting bracket 24 by any suitable means, for example by means of a threaded stud 22 and lock nuts 23. Bracket 24 is generally C-shaped, and has a clamping bolt 25 threaded through a hole in one arm and aligned with a clamping notch 26 in the other arm. Bracket 24 and hence the entire sensor assembly may be attached to a vertical rod of a mounting stand (not shown) at any desired height, then secured in place by tightening knob 27 which is attached to the end of clamping bolt 25. It will be appreciated that any other type of clamping or supporting means could be used in place of bracket 24 for the purpose of supporting the sensor assembly at the desired position during a surgical procedure.

Each of sensor blocks 20 and 21 have a number of holes formed therein as follows. Block 20 has a semicylindrical channel 30 formed therein along one edge, and block 21 has a complementary channel 31 which cooperates with channel 30 to form a drip chamber receiving bore 32, when the blocks are positioned together. Each of blocks 20 and 21 have a number of other bores formed therein as follows. Bores 34 and 35 are provided generally perpendicular to the drip chamber receiving area 32, for mounting the ultrasonic sensors. The portions of bores 34 and 35 adjacent drip chamber area 32 are of larger diameter than the outer portions.

The ultrasonic transducers 36 and 37 are positioned within the bores and seated against the annular step formed where bores 34 and 35 narrow in diameter. The open ends of bores 34 and 35 provide air backing for proper operation of the transducers. Transducers 36 and 37 are disc-shaped piezoelectric or piezoceramic crystals, and the inner portions of bores 34 and 35 are sized according to the diameter of these transducers for a good fit. The transducers are then held in place by fillings 38 and 39, which are layers of a polymeric material such as epoxy. The surfaces of the epoxy fillings facing inwards towards drip chamber receiving area 32 are convex, so as to protrude beyond the general curvature of channels 30 and 31 into the drip chamber receiving area 38. Polymeric fillings 38 and 39 serve four functions. They waterproof the silver surface of the transducer crystals to prevent corrosion from contact with saline solutions used in medical procedures, and they provide electrical insulation between the electronic circuitry and the tubing system which is in contact with the patient. The polymeric fillings also serve as an ultrasonic lens for focusing of the acoustic energy. It will be appreciated that the lens curvature could be concave, convex or flat as may be desired in a given application. Finally, the polymeric fillings provide a contact point for mechanical coupling of acoustic energy from the transducers to the drip chamber.

Lead wires attach to both sides of the ultrasonic transducers and the lead wire cables 40 and 41 are directed behind the transducers and out through holes in the sides of blocks 20 and 21. These cables are held in place by set screws 42 and 43 which are tapped into holes provided in the blocks, and which act as a strain relief to protect the delicate connections. Lead wire cables 40 and 41 are brought along the sides of sensor blocks 20 and 21 and are held in place thereon by the cable clamps 44 and 45 respectively.

A pair of push rods and a return spring are provided for clamping the sensor assembly about the drip chamber. A first push rod 50 passes through a clearance hole 53 provided in block 21 and is press fitted into a coaxially aligned hole in the facing portion of block 20. Similarly, a push rod 51 passes through a clearance hole 52 provided in block 20 and is press fitted into a coaxially aligned hole provided in block 21. A return spring 55 is provided in a pair of coaxially aligned bores in the two blocks, and is held in place by means of an enlarged diameter at one end 56 and by a retaining pin 57 at the other end, or by any other suitable means.

To put the sensor assembly in use, it is first mounted on a support by means of mounting bracket 24 and clamping bolt 25. Push rods 50 and 51 are then pushed towards each other with the fingers, thereby causing mounting blocks 20 and 21 to move apart. The drip chamber is then inserted in the receiving area 32, and the push rods are released. Return spring 55 then pulls the sensor blocks back together, with the protruding portions of fillings or lenses 38 and 39 contacting opposite sides of the drip chamber.

In the preferred embodiment, the electronic detection circuitry and the tube clamping means are housed in a common housing 12 for convenience, although separate housings could be used if desired. Any type of tube clamping means could be used, but it is preferable to use a spring-loaded fail safe type of clamp such as is disclosed in the previously mentioned U.S. Pat. No.

3,935,876. In this type of clamp, the mechanical force of a spring is used to actuate the clamp, while an electromagnet is used to oppose the spring to hold the clamp open, except when air or foam is detected at which time the electromagnet is shut off allowing the clamp to close. If there should be electrical power failure, the clamp will thus close to prevent further operation without benefit of the air leak detector.

Figure 4:
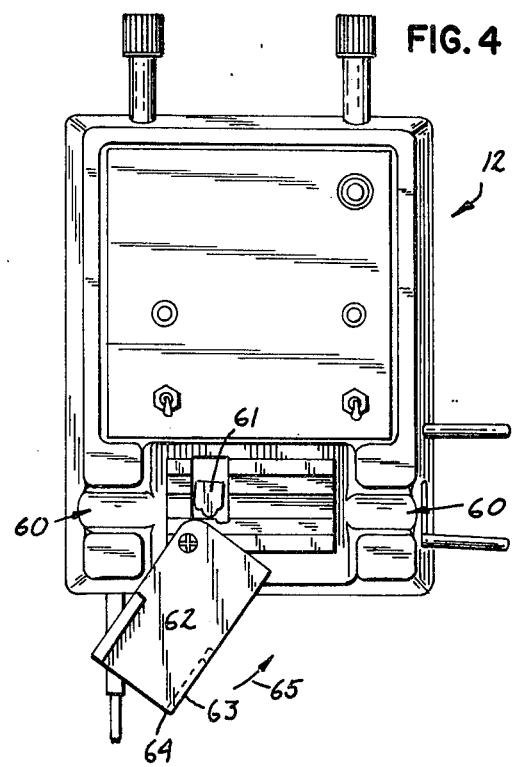
FIG. 4 is a view in top plan of the tube clamp and electronic chassis portion of the detector shown in FIG. 1.
Figure 5:
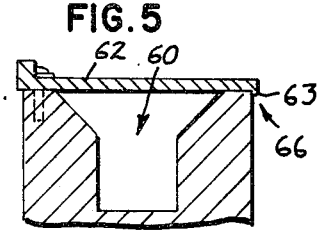
FIG. 5 is a fragmentary sectional detail of the tube receiving channel and cover door shown in FIGS. 1 and 4.

In FIG. 4, the housing 12 includes a tube receiving channel generally designated by reference number 60. A movable clamp head 61 cooperates with the edge of the members defining channel 60 to form the clamp. A cover 62 is pivotally attached by means of a bolt as indicated in FIGS. 4 and 5, for allowing insertion and removal of the tube from the channel 60, and for holding the tube in place during operation. Cover 62 is shown in its open position in FIG. 4 and in its closed position in FIG. 5. Cover 62 includes a lip 63 which is shown in phantom lines in FIG. 4. Lip 63 ends by being beveled or tapered approximately midway down the edge of the cover. Cover 62 is preferably made of plastic or some other semi-flexible material, so that when cover 62 is swung into the closed position as indicated by arrow 65, the tapered or beveled lips rides up and over the portion of the housing which defines channel 60, then snaps into place over the edge thereof as indicated at reference number 66 in FIG. 5. In this manner the blood tube may be held securely in place in the tube receiving channel.

Figure 6:
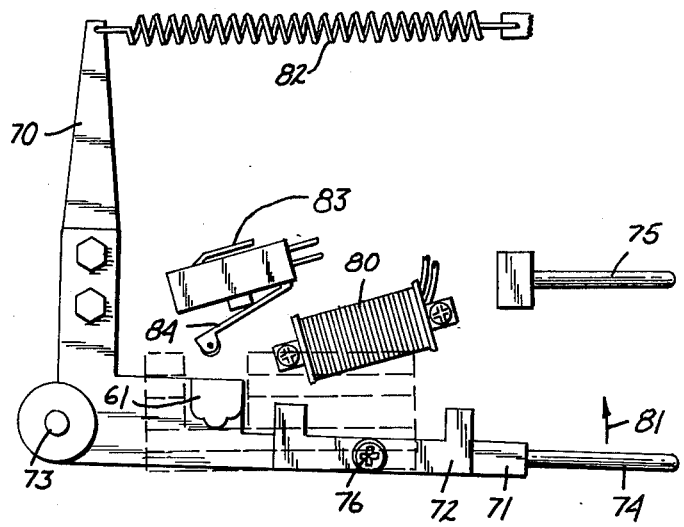
FIG. 6 is a diagrammatic view of the tube clamping mechanism used in the preferred embodiment of the present invention.

Referring to FIG. 6, the tube clamping means includes a generally L-shaped arm having a leg 70, and another leg 71 at approximately right angles thereto. A pivot bolt assembly 73 pivotally attaches arm 70–71 to the housing (not shown in FIG. 6). A handle 74 is provided on the end of leg 71, and a matching stationary handle 75 is affixed to the housing. Leg 71 has attached thereto a clamping head 61, and a C-shaped magnetic member 72, which is pivotally attached to leg 71 by means of a bolt 76 or any other suitable means. An electromagnet 80 is mounted in the housing in alignment with magnetic member 72, so that when handle 74 is pulled towards handle 75 as indicated by arrow 81, the ends of magnetic member 72 swing into contact with the ends of solenoid 80 to complete a magnetic circuit. A spring 82 connects from the end of leg 70 to the housing to normally urge the clamp closed, i.e., in the opposite direction from arrow 81. However, once the clamp has been opened, electrical energization of electromagnet 80 will magnetically hold the clamp open against the force of spring 82. When the current is released, the clamp will close, driving clamp head 61 towards the edge of the members which define the tube receiving channel 60 (shown in broken lines in FIG. 6), pinching the blood tube therebetween.

A microswitch 83 is mounted within the chassis and has an actuating lever 84 positioned for actuation by the back of clamp head 61 when the clamp is in its open position. This switch may be used through external connections to operate a blood pump or other device that needs to be cut off when the clamp closes.

Figure 7:
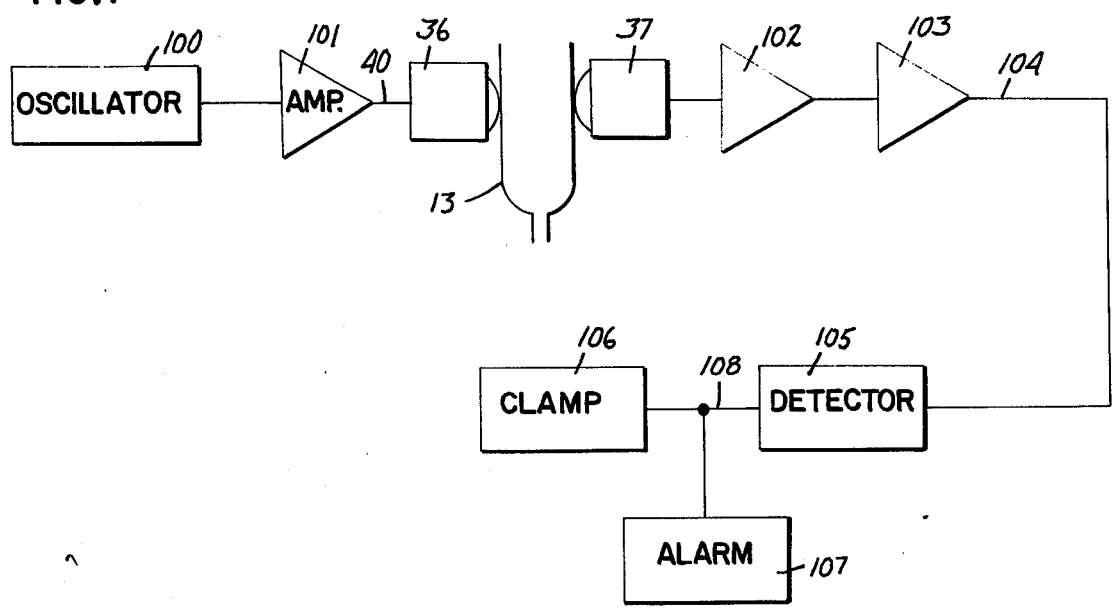
FIG. 7 is a block diagram of energization and detection circuitry for use in the present invention.

Referring now to FIG. 7, the electrical energization and detection circuitry is shown in block diagram. An oscillator 100 provides high frequency signals which are amplified by amplifier 101 and transmitted by lead 40 to transducer 36. In the preferred embodiment, the piezoelectric crystals are two megahertz crystals, which is also the frequency to which the oscillator is adjusted. The amplifiers in the system are designed to handle this frequency, as is generally known in the electronic amplifier art.

The other transducer 37 is indicated in FIG. 7 as being positioned on the opposite side of the symbolically indicated drip chamber 13. Transducer 37 connects to an amplifier 102 and optionally to a second cascaded amplifier 103 as may be required for providing sufficient signal strength. After amplification, the signals are applied via lead 104 to a level detector 105 which compares the received level to a predetermined quantity. If there is blood in the drip chamber above the level of the sensors, there will be provided a highly conductive ultrasonic path from one crystal, through its epoxy lens, the drip chamber and blood, the other epoxy lens, to the receiving crystal. A relatively large amplitude signal will then be received at detector 105. If, however, an excessive amount of air or foam is present between the transducers, the signal level will be markedly reduced since the air or foam is a relatively poor conductor of ultrasonic acoustic energy as compared to blood.

Detector 105 will provide an output signal at lead 108 indicative of whether excessive air or foam is present in the drip chamber. This output signal can be used to operate any desired type of audible or visual warning, and it can be tied into the controls for other devices for automatically stopping or altering the procedure. In the preferred embodiment, output signals on lead 108 are sent to an alarm device 107 and tube clamping means 106.

Figure 8:
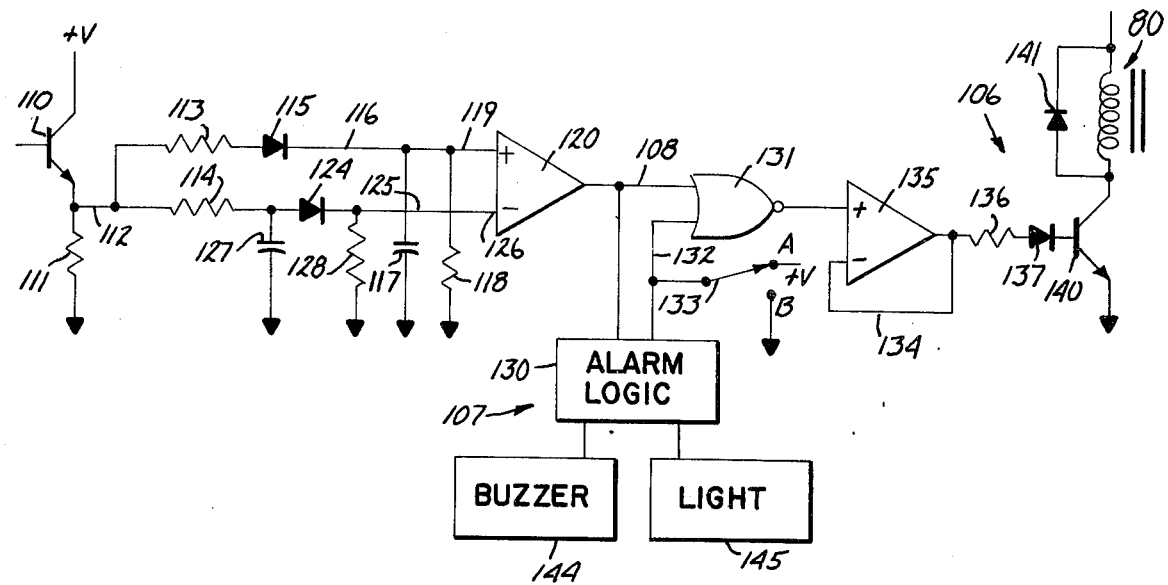
FIG. 8 is a schematic diagram of a presently preferred signal level detection circuit for use in the present invention.

Although many different types of signal level detectors can be used in conjunction with the present invention, FIG. 8 shows a specific type of level detector, clamp control and alarm control used in the preferred embodiment. In FIG. 8, reference number 119 indicates an output transistor of the last amplification stage of amplifier 103. The collector of transistor 119 is connected to a source of working direct current voltage indicated by +V. It will be appreciated that +V can be provided by a self-contained battery, or by a line operated power supply as is generally known in the art. The emitter of transistor 110 connects through a resistor 111 to signal ground. The emitter of transistor 110 also connects via a lead 112 to a pair of resistors 113 and 114.

The other side of resistor 113 connects through a diode 115 to a lead 116. A capacity 117 and a resistor 118 are connected between lead 116 and signal ground. Lead 116 connects to the noninverting input 119 of a comparator 120.

The other side of resistor 114 connects through a diode 124 to a lead 125 which connects to the inverting input 126 of comparator 120. A capacitor 127 is connected from resistor 114 to ground, and a resistor 128 connects from lead 125 to ground.

Comparator 120 may be an operational amplifier operated open-looped to achieve the voltage comparator function. It will be appreciated that power supply and ground connections for comparator 120 and for the other amplifiers and logic gates are provided, but are not shown in the Figures for purposes of clarity.

The output of comparator 120 is connected via lead 108 to the alarm logic network 130 and to one input of a NOR gate 131. The other input to NOR gate 131 is from a lead 132 which also connects to a switch 133 and to alarm logic 130. Switch 133 is the armed-bypass switch, and in the armed position (A), switch 133 connects lead 132 to +V. In the bypass position (B), switch 133 connects lead 132 to signal ground.

The output of NOR gate 131 connects to an amplifier 135 which has a direct feedback loop 134 to the inverting input to form a voltage follower. The output of amplifier 135 connects through a resistor 136 and a diode 137 to the base of a transistor 140. The emitter of transistor 140 connects to signal ground, and the collector connects through the magnet coil 80 to +V. A diode 141 is connected across magnet coil 80 for transient suppression.

In operation, drip chamber 13 is positioned within sensor assembly 11 (FIG. 1) and handle 74 is pulled toward handle 75 (FIGS. 4 and 6) to allow insertion of blood tube 15 in the tube receiving channel. At this point, switch 133 is in the bypass position, supplying a ground to gate 131. Transistor 140 will thus be ON energizing electromagnet 80, regardless of the state of comparator 102, so long as switch 133 is in the bypass position. The tube clamp will thus be held in the open position, and cover 62 can be snapped into place to hold the tube in the channel.

The bypass position is used for start-up operations since it is first necessary to purge air from this system and it is not desirable for the detector to be constantly trying to clamp off the tube during the start-up. In bypass mode, the alarm logic causes buzzer 144 to emit a buzz every minute to alert the medical personnel that the detector is in bypass mode.

Once air is purged from the system, switch 133 is switched to armed position, applying a logical high signal to one input of gate 131. In this condition, gate 131 is enabled, and the action of transistor 140 which controls electromagnet 80 will be controlled by comparator 120.

In FIG. 8, the output stage shown involving transistor 110 will have a DC bias with an AC signal superimposed thereon corresponding to the amplified received ultrasonic signals. This composite signal is sent through two paths to comparator 120. The lower path involves resistor 114 and capacitor 127 which comprise a low pass filter, essentially shunting the entire AC portion of the signal to ground and leaving only the DC bias. The upper path, comprising resistor 113, diode 115 and capacitor 117 comprises a half-wave rectifier, which responds to the DC bias plus the peaks of the superimposed AC signal, after half-wave rectification and filtering. This signal, which is applied to input 119, will ordinarily be larger than the DC bias signal which is applied to input 126. The relationship in magnitude between these signals, and hence the switching threshold of the detector, can be adjusted by selection of values for resistors 113 and 118, and resistors 114 and 128. Also, diode 124 can be used to match the voltage drop across half-wave rectifying diode 115. The component values are selected so that when the AC component of the composite waveform drops below a predetermined value, the input to input 119 drops below the input at 126, causing comparator 120 to switch from a high output to a low. This in turn causes gate 131 to switch to a low, and transistor 140 is cutoff causing the clamp to pinch off the flow. It will be appreciated that voltage following amplifier 135 is used to provide drive current for transistor 140, and may or may not be required depending upon the circuit design of gate 131.

In armed mode, alarm logic 130 provides rapid repeating signals from buzzer 144 and flashing light 145 through the duration of the air leak condition.

Figure 9:
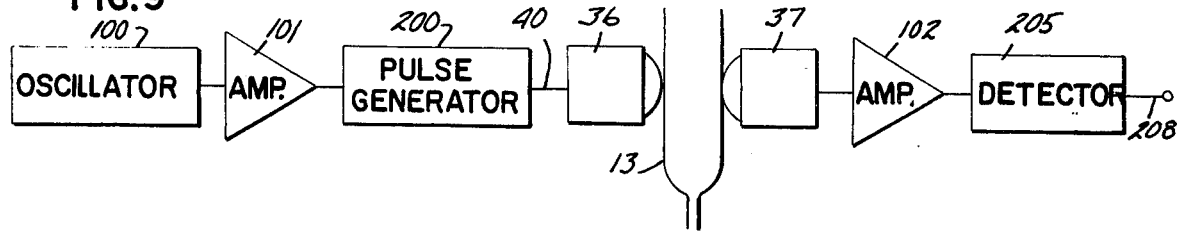
FIG. 9 is a block diagram of an alternate embodiment of an energization and detection circuit for use in the present invention.

FIG. 9 shows an alternate embodiment of the energization and detection circuitry of FIG. 7, which may use either a pulsed mode or a gated sinusoid mode of operation rather than a continuous wave mode. In FIG. 9, a pulse generating circuit 200 is connected between amplifier 101 and lead 40 which leads to transmit transducer 36. Pulse generator 200 periodically transmits pulses or bursts of ultrasonic energy through lead 40 to transmitter 36. Detector 205 performs essentially the same function which has previously been described with respect to detector 105, except that detector 205 of FIG. 9 is designed to be compatible with the pulse mode of operation. For example, detector 205 can be designed to be gated synchronously with pulse generator 200 to compare the received signal level to a predetermined level during the occurrence of a pulse, or it can be designed to measure the time averaged received signal level against a lower predetermined value selected in part by a consideration of the duty cycle of the pulses. An output is provided at terminal 208 for indicating when too low a signal is received, thus indicating presence of air or foam in the drip chamber. This signal can be used to operate clamping means or an alarm device as in FIG. 7.

Figure 10:
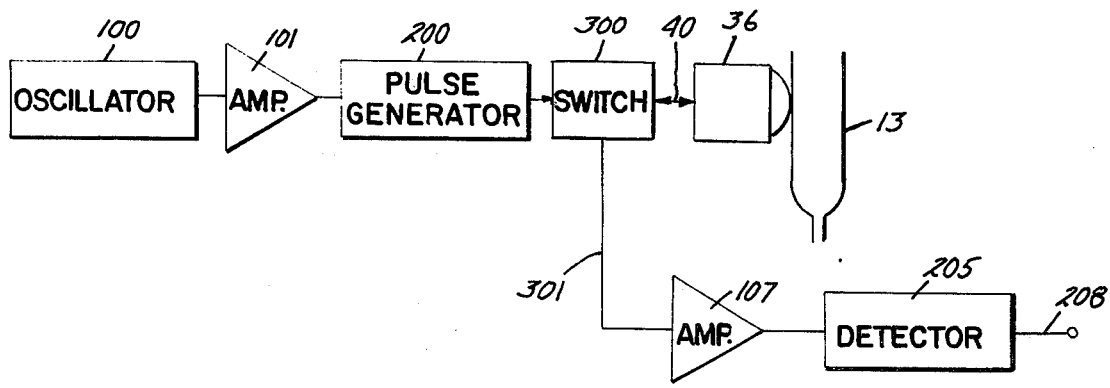
FIG. 10 is a block diagram showing another alternate energization and detection circuit for use in the present invention.

FIG. 10 shows another alternate embodiment of an energization and detection circuit, in which a single ultrasonic transducer 36 is used in an echo mode. For this mode, a sensor assembly can be used as in FIGS. 1, 2 and 3, except that only one of the sensor mounting blocks would contain an ultrasonic transducer. The other side may contain a reflective plate to reflect ultrasonic signals back through the drip chamber to the transducer, or alternatively the other block may be left blank and the system can work on reflections from the wall of the drip chamber. In FIG. 10, a multiplexing switch 300 is inserted between pulse generator 200 and lead 40 which connects to the ultrasonic transducer 36. Switch 300 also connects through a lead 301 to amplifier 107, and then to detector 205. When pulse generator 200 is to transmit a pulse, switch 300 conveys the pulse to transducer 36. Switch 300 then changes state to complete the path between lead 40 and lead 301. After the ultrasonic pulse has travelled through the drip chamber, bounced from the other side and returned to transducer 36, the received signal is transmitted through amplifier 107 to detector 205. Detector 205 compares the amplitude of the received pulse against a predetermined standard, and provides an output signal at terminal 208 indicating the presence of lack of air or foam in the drip chamber.

We claim:

1. An ultrasonic air and blood foam detector for use with a blood tube system including a drip chamber, comprising:
   a. ultrasonic sensing means adapted for positioning adjacent a blood drip chamber and having ultrasonic transducer means mounted within said sensing means and positioned for contact with said drip chamber;
   b. energization means connected to said transducer means for causing ultrasonic energy to be transmitted through said blood drip chamber;
   c. electronic signal detection means operatively connected to said transducer means for receiving signals transmitted through said blood drip chamber and operable in response to the signal level of the received ultrasonic signal to produce an output signal indicative of the presence of air or blood foam in said chamber; and d. said ultrasonic sensing means including a polymeric material lens on the surface of said ultrasonic transducer means for contact with the side of said drip chamber, said lens having a convex surface.

2. A detector according to claim 1 wherein said energization means is adapted for applying pulsed energization to said transducer means.

3. A detector according to claim 1 wherein said energization means is adapted for applying bursts of gated sinusoid wave energization to said transducer means.

4. A detector according to claim 1 wherein said energization means is adapted for providing continuous wave energization to said transducer means.

5. A detector according to claim 1 wherein said ultrasonic sensing means includes a single ultrasonic transducer and further including switching means for alternately connecting said transducer to said energization means and to said electronic signal level detection means, whereby ultrasonic energy may be received after transmission through the blood drip chamber and reflection back to the transducer.

6. A detector according to claim 1 further including tube clamp means for positioning adjacent a blood tube associated with said drip chamber, and connected to said signal level detection means, said tube clamp means operable for selectively clamping the tube to prevent flow therethrough in response to said output signal when said output signal indicates the presence of air or blood foam in the drip chamber.

7. An ultrasonic air and blood foam detector for use with a blood tube system including a drip chamber comprising:
  a. a sensor housing adapted for positioning adjacent a blood drip chamber;
  b. a pair of ultrasonic transducers mounted in said housing for positioning against opposite sides of the drip chamber;
  c. tube clamp means comprising means defining a tube receiving channel, a pair of tube clamp members positioned on opposite sides of said channel, a movable actuator arm mounting one of said tube clamp members, spring bias means connected to said actuator arm for urging said tube clamp towards a closed position, and means for selectively holding said actuator arm in an open position;
  d. energization means connected to one of said transducers for causing ultrasonic acoustic energy to be transmitted therefrom through the drip chamber;
  e. amplifier means connected to the other of said transducers for amplifying signals transmitted through the drip chamber and received by said transducer;
  f. signal level detection means connected to said amplifier means, for detecting the level of the received signals;
  g. switching means connected to said signal level detection means and to said means for selectively holding said actuator arm, said switching means operable to cause release of said actuator arm to clamp said tube when a predetermined signal level is detected indicating presence of air or blood foam in the drip chamber; and
  h. acoustic lens members attached to the pair of ultrasonic transducers for contact with the sides of the drip chamber, said acoustic lens members comprising layers of polymeric material on said transducers.

8. A detector according to claim 7 wherein said acoustic lens members have a convex configuration.

9. A detector according to claim 8 wherein said energization means is adapted for providing continuous wave energization to said one transducer.

10. An ultrasonic air and blood foam detector for use with a blood tube system including a drip chamber, comprising:
  a. an ultrasonic sensor assembly including a pair of sensor body members, means slideably interconnecting said members for permitting relative motion of said members towards and away from each other, said sensor body members configured to form a drip chamber receiving area therebetween, and an ultrasonic transducer crystal mounted in at least one of said body members and positioned for contacting the side of a blood drip chamber when positioned in said receiving area;
  b. energization means connected to said sensor assembly for causing ultrasonic energy to be transmitted through said blood drip chamber; and
  c. electronic signal level detection means operatively connected to said sensor assembly for receiving signals transmitted through said blood drip chamber and operable in response to the signal level of the received ultrasonic signals to produce an output signal indicative of the presence of air or blood foam in said chamber.

11. A detector according to claim 10 further including tube clamp means for positioning adjacent a blood tube associated with the blood drip chamber, and connected to said electronic signal level detection means, said tube clamp means operable for selectively clamping the tube to prevent flow therethrough in response to said output signal.

12. A detector according to claim 10 wherein said ultrasonic sensor assembly further includes a polymeric material layer on said crystal shaped to form a lens for ultrasonic energy and positioned for contacting the side of a blood drip chamber when positioned in said receiving area.

13. A detector according to claim 10 wherein said ultrasonic sensor assembly includes a pair of ultrasonic transducer crystals, one mounted in each of said sensor body members, and wherein said energization means is connected to one of said transducer crystals, and said electronic signal level detection means is connected to the other of said transducer crystals.

14. A detector according to claim 10 wherein said energization means is adapted for applying pulsed energization to said ultrasonic sensor assembly.

15. A detector according to claim 10 wherein said energization means is adapted for providing bursts of gated sinusoidal wave energization to said ultrasonic sensor assembly.

16. A detector according to claim 10 wherein said energization means is adapted for providing continuous wave energization to said ultrasonic sensor assembly.

17. A detector according to claim 10 further including switching means for alternately connecting said ultrasonic transducer crystal to said energization means and to said electronic signal level detection means, whereby ultrasonic energy may be received after transmission through the blood drip chamber and reflection back to the transducer crystal.

* * * * *

UNITED STATES PATENT AND TRADEMARK OFFICE
CERTIFICATE OF CORRECTION

PATENT NO. : 4,068,521
DATED : January 17, 1978
INVENTOR(S) : Louis C. Cosentino and LeRoy J. Fischbach It is certified that error appears in the above-identified patent and that said Letters Patent are hereby corrected as shown below:

Column 4, line 17, after "area" delete "38." and insert --32.--

Column 5, line 24, "lips" should be --lip--

Column 6, line 35, "119" should be --110--

Column 6, line 37, "119" should be --110--

Column 8, line 66, "signal" should be --signals--

Signed and Sealed this

Twenty-third Day of May 1978

[SEAL]

Attest:

RUTH C. MASON
Attesting Officer

LUTRELLE F. PARKER
Acting Commissioner of Patents and Trademarks